US008821900B2

(12) United States Patent
Tani et al.

(10) Patent No.: US 8,821,900 B2
(45) Date of Patent: Sep. 2, 2014

(54) ANTI-ADHESION MATERIAL

(75) Inventors: Toru Tani, Shiga (JP); Sumihiro Kamitani, Shiga (JP); Tomokazu Mukai, Kanagawa (JP)

(73) Assignees: Kawasumi Laboratories, Inc., Oita (JP); Shiga University of Medical Science, Shiga (JP)

( * ) Notice: Subject to any disclaimer, the term of this patent is extended or adjusted under 35 U.S.C. 154(b) by 0 days.

(21) Appl. No.: 13/519,742

(22) PCT Filed: Dec. 27, 2010

(86) PCT No.: PCT/JP2010/073631
§ 371 (c)(1),
(2), (4) Date: Jun. 28, 2012

(87) PCT Pub. No.: WO2011/081162
PCT Pub. Date: Jul. 7, 2011

(65) Prior Publication Data
US 2012/0301515 A1    Nov. 29, 2012

(30) Foreign Application Priority Data
Dec. 28, 2009   (JP) .................................. 2009-296876

(51) Int. Cl.
*A61K 9/00*      (2006.01)
*B32B 33/00*     (2006.01)
*A61L 31/10*     (2006.01)
*A61L 31/14*     (2006.01)

(52) U.S. Cl.
CPC .............. *A61L 31/10* (2013.01); *A61L 31/148* (2013.01)
USPC ........................................ 424/400; 428/336

(58) Field of Classification Search
USPC .......................................... 424/400; 428/336
See application file for complete search history.

(56) References Cited

U.S. PATENT DOCUMENTS

2007/0134288 A1 *  6/2007  Parsonage et al. ............ 424/423
2008/0254091 A1 * 10/2008  Lee et al. ...................... 424/423

FOREIGN PATENT DOCUMENTS

| JP | H05-508161 A | 11/1993 |
| JP | H06-508169 A | 9/1994 |
| JP | 2003-62063 A | 3/2003 |
| JP | 2003-126235 A | 5/2003 |
| JP | 2004-209228 A | 7/2004 |
| JP | 2007-268239 A | 10/2007 |
| JP | 2008-109979 A | 5/2008 |
| JP | 2009-506861 A | 2/2009 |
| JP | 2010-279574 A | 12/2010 |
| WO | 2005/094915 A1 | 10/2005 |
| WO | 2006/100895 A1 | 9/2006 |

OTHER PUBLICATIONS

NOAA. Aerosol Optical Thickness Products. Jul. 31, 2012. p. 1.*
English Translation of Written Opinion (PCT/ISA/237) of the International Searching Authority, issued on Feb. 1, 2011 in corresponding International Application No. PCT/JP2010/073631.
International Search Report (PCT/ISA/210), dated Feb. 1, 2011, issued by the International Searching Authority in corresponding International Application No. PCT/JP2010/073631.
Written Opinion (PCT/ISA/237) of the International Searching Authority, issued on Feb. 1, 2011 in corresponding International Application No. PCT/JP2010/073631.
Kamitani, Sumihiro et al., "OP-082-7 Development of Novel Anti-Adhesion Material," Journal of Japan Surgical Society, vol. 111, Special Issue No. 2, Mar. 5, 2010, 8 pages.

* cited by examiner

*Primary Examiner* — Frederick Krass
*Assistant Examiner* — Tracy Liu
(74) *Attorney, Agent, or Firm* — Sughrue Mion, PLLC (57) ABSTRACT

An object of the present invention is to provide an anti-adhesion material having sufficient in vivo degradability and excellent anti-adhesion characteristics, and also superior to conventional ones in terms of handling properties under wet conditions. The anti-adhesion material (1) of the present invention has a sheet-like base layer (10) containing a water soluble polymer (e.g., pullulan), a first cover layer (20) placed on a surface on one side of the base layer (10) and containing an aliphatic ester, and a second cover layer (30) placed on a surface on the other side of the base layer (10) and containing an aliphatic ester. The optical thickness of each of the first cover layer (20) and the second cover layer (30) is set to be 27 nm or greater and smaller than 160 nm.

12 Claims, 6 Drawing Sheets

ANTI-ADHESION MATERIAL

TECHNICAL FIELD

The present invention relates to an anti-adhesion material.

BACKGROUND ART

Anti-adhesion materials making use of a water soluble polymer such as hyaluronic acid are known as a conventional anti-adhesion material for reducing adhesion of body tissues which may occur after surgical operation, injury, or the like (see, e.g., Patent Documents 1 and 2).

Since conventional anti-adhesion materials make use of a water soluble polymer such as hyaluronic acid, they serve as an anti-adhesion material excellent in biocompatibility and in vivo degradability.

In addition, an anti-adhesion material obtained by forming a support layer on an adhesion layer to be attached to an application site of a living body is known as another conventional anti-adhesion material (see, e.g., Patent Documents 3 to 5).

RELATED ART DOCUMENTS

Patent Documents

Patent Document 1: JP 5-508161 A
Patent Document 2: JP 6-508169 A
Patent Document 3: JP 2003-126235 A
Patent Document 4: JP 2004-209228 A
Patent Document 5: JP 2008-109979 A

SUMMARY OF THE INVENTION

Problems to be Solved by the Invention

The conventional anti-adhesion materials disclosed in Patent Documents 1 and 2 are extremely inferior in terms of handling properties under wet conditions, for example, they are difficult to treat with wet tweezers during operation, because the water soluble polymer such as hyaluronic acid contained in the material is hydrophilic (water soluble). When the anti-adhesion material is inferior in terms of handling properties under wet conditions, it cannot be applied again once it has been applied to a position away from an intended position. This may lead to an increase in economic loss. In addition to these problems, a surgical instrument needs to be completely dried, which may put an excessive burden to users.

On the other hand, the another conventional anti-adhesion material disclosed in Patent Documents 3 to 5 have a support layer so that compared with anti-adhesion materials composed only of a base layer containing a water soluble polymer, it is expected to have improved handling properties under wet conditions. From the standpoint of in vivo degradability or anti-adhesion characteristics, however, it is difficult to say that the material fully reaches the required level.

The present invention has therefore been made to address such problems, and an object thereof is to provide an anti-adhesion material having sufficient in vivo degradability and excellent anti-adhesion characteristics, and also superior to conventional ones in terms of handling properties under wet conditions.

Means for Solving the Problems

[1] The anti-adhesion material according to the present invention has a base layer containing a water soluble polymer and a cover layer containing an aliphatic ester and placed on at least one of both surfaces of the base layer, an optical thickness of the cover layer, as measured using a spectroscopic ellipsometer with a wavelength of 380 nm to 900 nm, being 27 nm or greater and smaller than 160 nm.

The anti-adhesion material according to the present invention shows improved handling properties under wet conditions compared with anti-adhesion materials composed only of a base layer containing a water soluble polymer, because a cover layer containing an aliphatic ester is placed on at least one of both surfaces of the base layer containing a water soluble polymer. In addition, the optical thickness of the cover layer is set to be very small, which is 27 nm or greater and smaller than 160 nm, so that the presence of the cover layer does not reduce the in vivo degradability or anti-adhesion characteristics below the required level. Although the anti-adhesion material of the present invention will be described later in detail in Examples, it satisfies the required level of in vivo degradability and also has anti-adhesion characteristics comparable to that of an anti-adhesion material composed only of a base layer containing a water soluble polymer.

Accordingly, the anti-adhesion material of the present invention has sufficient in vivo degradability and excellent anti-adhesion characteristics, and is also superior to those of the conventional ones in terms of handling properties under wet conditions.

The test made by the present inventors has revealed that by setting the optical thickness of a cover layer to 27 nm or greater and smaller than 160 nm, the resulting anti-adhesion material not only can provide the above-described advantages but also can significantly improve the adhesion between the anti-adhesion material and body tissues when the anti-adhesion material is applied to the body tissues, as compared with the conventional ones.

[1] In the anti-adhesion material as described above in [1], it is advantageous to set the optical thickness of the cover layer to be 27 nm or greater but not greater than 128 nm.

Details will be described later in Examples, but such a configuration makes it possible to provide an anti-adhesion material having excellent anti-adhesion characteristics, superior to conventional ones in terms of handling properties under wet conditions, and having further improved in vivo degradability.

Moreover, from the standpoint of adhesion between the anti-adhesion material and the body tissues when the anti-adhesion material is applied to the body tissues, such a configuration makes it possible to provide an anti-adhesion material showing improved adhesion.

[3] The anti-adhesion material according to the present invention may be obtained by forming, on at least one of both surfaces of a base layer containing a water soluble polymer, a cover layer containing an aliphatic ester such that the layer thickness of the cover layer is 130 nm or greater and smaller than 820 nm.

Such a configuration makes it possible to provide an anti-adhesion material showing improved handling properties under wet conditions compared with anti-adhesion materials composed only of a base layer containing a water soluble polymer, because a cover layer containing an aliphatic ester is placed on at least one of both surfaces of a base layer containing a water soluble polymer. In addition, the cover layer is formed so as to adjust the layer thickness thereof to 130 nm or greater and smaller than 820 nm so that the cover layer becomes very thin and as a result, the presence of the cover layer does not reduce the in vivo degradability or anti-adhesion characteristics below the required level. Although details will be described later in Examples, the anti-adhesion material of the present invention fully satisfies the required level of in vivo degradability and in addition, it has anti-adhesion characteristics comparable to that of anti-adhesion materials composed only of a base layer containing a water soluble polymer.

The anti-adhesion material of the present invention therefore has sufficient in vivo degradability and excellent anti-adhesion characteristics, and is superior to conventional ones in terms of handling properties under wet conditions.

In addition, when the layer thickness of the cover layer is set to be 130 nm or greater and smaller than 820 nm, the resulting anti-adhesion material not only produces the above-described advantage, but also can be applied to the body tissue with markedly improved adhesion between the anti-adhesion material and the body tissues compared with conventional anti-adhesion materials.

[4] In the anti-adhesion material as described above in [3], it is advantageous to set the layer thickness of the cover layer to be 130 nm or greater but not greater than 660 nm.

Such a configuration makes it possible to provide an anti-adhesion material having excellent anti-adhesion characteristics, superior to conventional ones in terms of handling properties under wet conditions, and having further improved in vivo degradability.

Moreover, also from the standpoint of adhesion between the anti-adhesion material and body tissues when the anti-adhesion material is applied to the body tissues, such a configuration makes it possible to provide an anti-adhesion material showing improved adhesion.

[5] In the anti-adhesion material as described above in any one of [1] to [4], it is advantageous that the cover layer has a first cover layer placed on one of the surfaces of the base layer and a second cover layer placed on another of the surfaces of the base layer, and that the first cover layer and the second cover layer are made of same material.

Such a configuration makes it possible to provide an anti-adhesion material with an improved production efficiency at a reduced production cost.

[6] In the anti-adhesion material as described above in any one of [1] to [4], it is advantageous that the cover layer has a first cover layer placed on one of the surfaces of the base layer and a second cover layer placed on another of the surfaces of the base layer, and that the first cover layer and the second cover layer are made of different materials.

Such a configuration makes it possible to provide an anti-adhesion material having different functions between two surfaces.

[7] In the anti-adhesion material as described above in any one of [1] to [6], it is advantageous that at least one of the base layer and the cover layer contains a medical agent.

Such a configuration makes it possible to provide an anti-adhesion material further having the efficacy of the medical agent.

[8] In the anti-adhesion material as described above in any one of [1] to [7], polysaccharides, proteins or synthetic polymers may be used advantageously as the water soluble polymer.

Advantage of the Invention

Owing to an anti-adhesion material of the present invention, it possible to provide an anti-adhesion material having sufficient in vivo degradability and excellent anti-adhesion characteristics, and superior to conventional ones in terms of handling properties under wet conditions.

BRIEF DESCRIPTION OF DRAWINGS

FIG. 1 includes diagrams for describing an anti-adhesion material 1 according to a first embodiment, in which FIG. 1(a) is a perspective view of the anti-adhesion material 1 and FIG. 1(b) is a partially enlarged cross-sectional view of the material;

FIG. 2 includes diagrams for describing an anti-adhesion material 2 according to a second embodiment, in which FIG. 2(a) is a perspective view of the anti-adhesion material 2 and FIG. 2(b) is a partially enlarged cross-sectional view of the material;

FIG. 3 includes diagrams for describing an anti-adhesion material 3 according to a third embodiment, in which FIG. 3(a) is a perspective view of the anti-adhesion material 3 and FIG. 3(b) is a partially enlarged cross-sectional view of the material;

FIG. 4 includes diagrams for describing an anti-adhesion material 4 according to a fourth embodiment, in which FIG. 4(a) is a perspective view of the anti-adhesion material 4 and FIG. 4(b) is a partially enlarged cross-sectional view of the material;

EMBODIMENTS OF THE INVENTION

Hereinafter, an anti-adhesion material of the present invention will be described based on embodiments shown in the above diagrams.

First Embodiment

Figure 1:
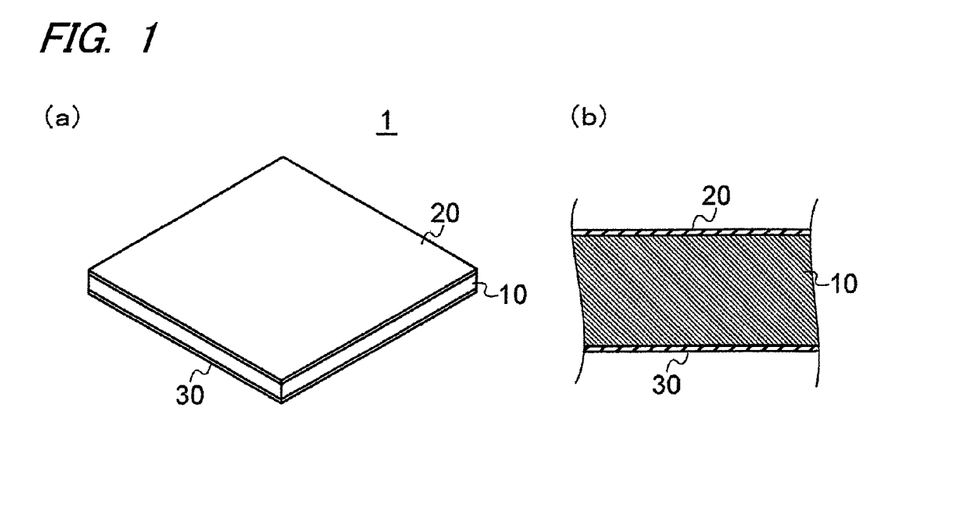

FIG. 1 includes diagrams for describing an anti-adhesion material 1 according to a first embodiment, in which FIG. 1(a) is a perspective view of the anti-adhesion material 1 and FIG. 1(b) is a partially enlarged cross-sectional view of the anti-adhesion material 1. In FIGS. 1(a) and 1(b), the layer thickness of the base layer 10 and the layer thicknesses of the first cover layer 20 and the second cover layer 30 relative to the base layer 10 are exaggerated to some extent to facilitate understanding of the present invention.

The anti-adhesion material 1 according to the first embodiment has a sheet-like base layer 10, a first cover layer 20 placed on a surface on one side of the base layer 10, and a second cover layer 30 placed on a surface on the other side of the base layer 10.

The base layer 10 is composed of a water soluble polymer. As the water soluble polymer, polysaccharides, proteins and synthetic polymers can be preferably used.

Preferred examples of the polysaccharides include storage polysaccharides of animals or plants such as starch, amylose, amylopectin, glycogen, glucomannan, dextrin, glucan, and fructan; structural polysaccharides of animals or plants such as cellulose, pectin, and chitin; polysaccharides derived from sea weeds such as carrageenan and agarose; microorganism polysaccharides such as pullulan, plant gum polysaccharides such as locust bean gum and guar gum; glycosaminoglycans such as heparin, hyaluronic acid, chondroitin sulfate, haparan sulfate, dermatan sulfate, and keratan sulfate; and derivatives of these polysaccharides.

Preferred examples of the proteins include gelatin, casein, and collagen.

Preferred examples of the synthetic polymers include polyvinyl alcohol, polyvinyl alcohol derivatives, polyacrylic acid-based water soluble polymers, polyacrylamide, polyacrylamide derivatives, polyethylene oxide, polyethylene oxide derivatives, polyvinylpyrrolidone, polyvinylpyrrolidone derivatives, polyamide-based polymers, polyalkylene oxide-based polymers, polyether glycol-based polymers, and maleic anhydride copolymer-based polymers.

From the standpoint of improving the flexibility of the entire anti-adhesion material, pullulan is particularly preferred among the water soluble polymers exemplified above.

The layer thickness of the base layer 10 is set to be, for example, 1 μm to 5000 μm.

The first cover layer 20 and the second cover layer 30 as the cover layer are both composed of an aliphatic ester. Preferred examples of the aliphatic ester include poly(lactide)s, poly(glycolide)s, poly(lactide-co-glycolide)s, poly(lactic acid)s, poly(glycolic acid)s, poly(lactic acid-co-glycolic acid)s, polycaprolactones, polycarbonates, polyesteramides, polyanhydrides, poly(amino acid)s, polyorthoesters, polyacetals, polycyanoacrylates, polyetheresters, poly(dioxanone)s, poly(alkylene alkylate)s, copolymers of polyethylene glycol and polyorthoester, biodegradable polyurethane mixtures, copolymers of the above-described esters, and polymer alloys. Using at least one of poly(lactic acid)s, poly(glycolic acid)s, polycaprolactones, polycarbonates, and copolymers of the above-described esters is particularly preferred because they are excellent in biocompatibility and in vivo degradability. It is to be noted that in the first embodiment, the first cover layer 20 and the second cover layer 30 are made of the same material selected from the materials exemplified above.

The first cover layer 20 has an optical thickness of 27 nm or greater and smaller than 160 nm as measured using a spectroscopic ellipsometer with a wavelength of 380 nm to 900 nm. Similar to the first cover layer, the second cover layer 30 has an optical thickness of 27 nm or greater and smaller than 160 nm as measured using a spectroscopic ellipsometer with a wavelength of 380 nm to 900 nm.

The optical thickness of each of the first cover layer 20 and the second cover layer 30 as measured using a spectroscopic ellipsometer with a wavelength of 380 nm to 900 nm is more preferably 27 nm or greater but not greater than 128 nm.

The term "optical thickness" as used herein means a thickness determined by optically measuring an object to be measured. On the other hand, the term "layer thickness" means a thickness determined by physically measuring an object to be measured. "Optical thickness" and "layer thickness" are used herein as terms different in meaning.

The anti-adhesion material 1 according to the first embodiment can be manufactured by carrying out "base layer preparation step" and "cover layer forming step" in the order of mention. These steps will hereinafter be described specifically.

"Base Layer Preparation Step"

First, a base layer 10 of a predetermined size is prepared. As the material of the base layer 10, materials exemplified above can be used preferably.

"Cover Layer Forming Step"

Next, a first cover layer 20 is formed on one of the surfaces of the base layer 10 thus prepared and a second cover layer 30 is formed on the other surface of the base layer 10. With regard to the layer forming method of the first cover layer 20 and the second cover layer 30, the first cover layer 20 and the second cover layer 30 can be formed on the base layer 10, for example, by preparing a coating solution containing the material of the first cover layer 20 and the second cover layer 30 at a predetermined concentration, dipping the base layer 10 in the resulting coating solution for a predetermined period of time, taking it out from the coating solution, and then drying it.

In the anti-adhesion material 1 according to the first embodiment, the first cover layer 20 is formed such that its layer thickness becomes 130 nm or greater and smaller than 820 nm. Similarly, the second cover layer 30 is formed such that its layer thickness becomes 130 nm or greater and smaller than 820 nm.

It is more advantageous to form each of the first cover layer 20 and the second cover layer 30 such that the layer thickness becomes 130 nm or greater but not greater than 660 nm, respectively.

The anti-adhesion material 1 of the first embodiment having such a configuration has the first cover layer 20 and the second cover layer 30 each containing an aliphatic ester on both surfaces of the base layer 10 containing a water soluble polymer, so it shows improved handling properties under wet conditions compared with anti-adhesion materials composed only of a base layer containing a water soluble polymer. In addition, since the optical thickness of each of the first cover layer 20 and the second cover layer 30 as measured using a spectroscopic ellipsometer with a wavelength of 380 nm to 900 nm is set to be very small, which is 27 nm or greater and smaller than 160 nm (130 nm or greater but not greater than 820 nm in terms of the layer thickness when formed as a layer), presence of the first cover layer 20 and the second cover layer 30 does not reduce the in vivo degradability or anti-adhesion characteristics below the required level. Although details will be described later in Examples, the anti-adhesion material 1 according to the first embodiment fully satisfies the level of in vivo degradability and in addition, it has anti-adhesion characteristics comparable to that of anti-adhesion materials composed only of a base layer containing a water soluble polymer.

The anti-adhesion material 1 according to the first embodiment therefore has sufficient in vivo degradability and excellent anti-adhesion characteristics, and is also superior to conventional ones in terms of handling properties under wet conditions.

Although details will be described later in Examples, since the optical thickness of each of the first cover layer 20 and the second cover layer 30 is 27 nm or greater and smaller than 160 nm (130 nm or greater and smaller than 820 nm in terms of the layer thickness when formed as a layer), the anti-adhesion material 1 according to the first embodiment not only produces the above-described advantage but also can significantly improve the adhesion between the anti-adhesion material 1 and body tissues when the anti-adhesion material 1 is applied to the body tissues, compared with the conventional anti-adhesion materials.

Moreover, the anti-adhesion material 1 according to the first embodiment is in a form of a sheet so that it can be used widely regardless of the site of the body tissue to be applied.

In the anti-adhesion material 1 according to the first embodiment, the first cover layer 20 and the second cover layer 30 are made of the same material, which makes it possible to improve a production efficiency and reduce a production cost.

Second Embodiment

Figure 2:
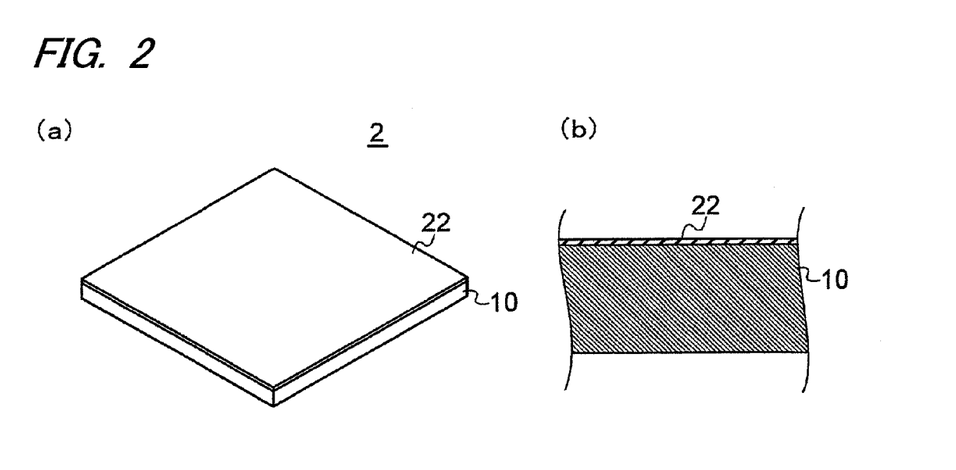

FIG. 2 includes diagrams for describing an anti-adhesion material 2 according to a second embodiment, in which FIG. 2(*a*) is a perspective view of the anti-adhesion material 2 and FIG. 2(*b*) is a partially enlarged cross-sectional view of the anti-adhesion material 2. In FIGS. 2(*a*) and 2(*b*), the layer thickness of the base layer 10 and the layer thickness of a cover layer 22 relative to the base layer 10 are exaggerated to some extent to facilitate understanding of the present invention. In FIG. 2, members similar to those in FIG. 1 are identified by the same reference number and a detailed description is omitted.

The anti-adhesion material 2 according to the second embodiment has, in principle, a similar configuration to that of the anti-adhesion material 1 according to the first embodiment but is different from the anti-adhesion material 1 according to the first embodiment in that a cover layer is placed only on the surface on one side of the base layer.

Described specifically, the anti-adhesion material 2 according to the second embodiment has, as shown in FIG. 2, a sheet-like base layer 10 and a cover layer 22 placed on a surface on one side of the base layer 10.

The cover layer 22 is made of an aliphatic ester. Examples of the aliphatic ester are similar to those exemplified for the first cover layer 20 and the second cover layer 30 described in the first embodiment.

The optical thickness of the cover layer 22 as measured using a spectroscopic ellipsometer with a wavelength of 380 nm to 900 nm is set to be 27 nm or greater and smaller than 160 nm (130 nm or greater and smaller than 820 nm in terms of the layer thickness when formed as a layer).

The optical thickness of the cover layer 22 as measured using a spectroscopic ellipsometer with a wavelength of 380 nm to 900 nm is more preferably 27 nm or greater but not greater than 128 nm (130 nm or greater but not greater than 660 nm in terms of the layer thickness when formed as a layer).

Thus, the anti-adhesion material 2 according to the second embodiment is different from the anti-adhesion material 1 according to the first embodiment in that a cover layer is placed only on the surface on one side of the base layer. Since the cover layer 22 containing an aliphatic ester is placed on the surface on one side of the base layer 10 containing a water soluble polymer, however, the resulting anti-adhesion material shows, similar to the anti-adhesion material 1 according to the first embodiment, improved handling properties under wet conditions compared with anti-adhesion materials composed only of a base layer containing a water soluble polymer. In addition, the optical thickness of the cover layer 22 as measured using a spectroscopic ellipsometer with a wavelength of 380 nm to 900 nm is set to be very small, which is 27 nm or greater and smaller than 160 nm (130 nm or greater and smaller than 820 nm in terms of the layer thickness when formed as a layer), so that the anti-adhesion material thus obtained has in vivo degradability satisfying the required level and at the same time, has anti-adhesion characteristics comparable to that of anti-adhesion materials composed only of a base layer containing a water soluble polymer.

The anti-adhesion material 2 according to the second embodiment therefore has sufficient in vivo degradability and excellent anti-adhesion characteristics, and is also superior to conventional ones in terms of handling properties under wet conditions.

The anti-adhesion material 2 according to the second embodiment has a similar configuration to that of the anti-adhesion material 1 according to the first embodiment except that a cover layer is placed only on the surface on one side of the base layer so that it has any relevant advantages among the advantages which the anti-adhesion material 1 according to the first embodiment has.

Third Embodiment

Figure 3:
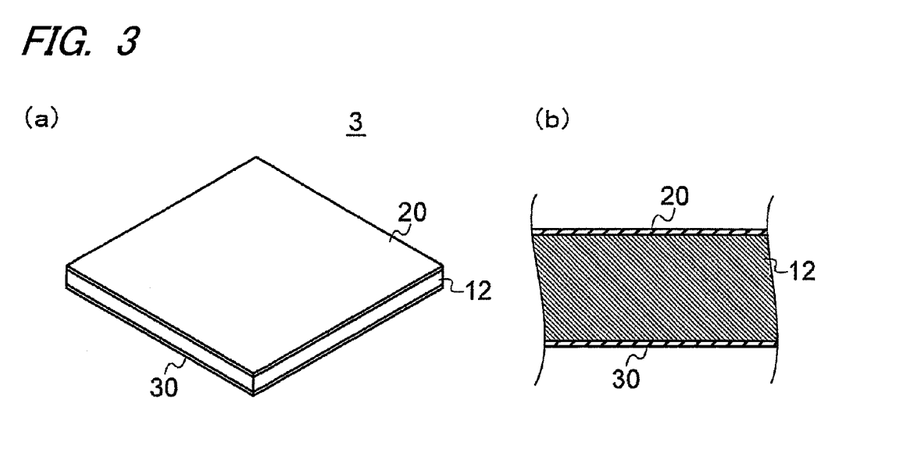

FIG. 3 include diagrams for describing an anti-adhesion material 3 according to a third embodiment, in which FIG. 3(*a*) is a perspective view of the anti-adhesion material 3 and FIG. 3(*b*) is a partially enlarged cross-sectional view of the anti-adhesion material 3. In FIGS. 3(*a*) and 3(*b*), the layer thickness of a base layer 12 and the layer thicknesses of the first cover layer 20 and the second cover layer 30 relative to the base layer 12 are exaggerated to some extent to facilitate understanding of the present invention. In FIG. 3, members similar to those in FIG. 1 are identified by the same reference number and a detailed description is omitted.

The anti-adhesion material 3 according to the third embodiment has, in principle, a configuration very similar to that of the anti-adhesion material 1 according to the first embodiment, but is different from the anti-adhesion material 1 according to the first embodiment in that the base layer contains an antibacterial agent.

Described specifically, the anti-adhesion material 3 according to the third embodiment has, as the base layer thereof, a base layer 12 containing an antibacterial agent as shown in FIG. 3. The base layer 12 is made of a water soluble polymer to which an antibacterial agent has been added.

Examples of the water soluble polymer forming the base layer 12 are similar to those exemplified for the base layer 10 in the first embodiment. As the antibacterial agent, for example, new quinolone-based antibacterial agents can be used preferably.

The layer thickness of the base layer 12 is set to be, for example, 1 μm to 5000 μm.

Thus, the anti-adhesion material 3 according to the third embodiment is different from the anti-adhesion material 1 according to the first embodiment in that the base layer contains an antibacterial agent. Since the first cover layer 20 and the second cover layer 30 containing an aliphatic ester are placed on both surfaces of the base layer 12 containing a water soluble polymer, respectively, however, the resulting anti-adhesion material has, similar to the anti-adhesion material 1 according to the first embodiment, improved handling properties under wet conditions compared with anti-adhesion materials composed only of a base layer containing a water soluble polymer. In addition, the optical thickness of the first cover layer 20 and the second cover layer 30 as measured using a spectroscopic ellipsometer with a wavelength of 380 nm to 900 nm is set to be very small, which is 27 nm or greater and smaller than 160 nm (130 nm or greater and smaller than 820 nm in terms of the layer thickness when formed as a layer), so that the resulting anti-adhesion material has in vivo degradability sufficiently satisfying the required level and at the same time, has anti-adhesion characteristics comparable to that of anti-adhesion materials composed only of a base layer containing a water soluble polymer.

The anti-adhesion material 3 according to the third embodiment therefore has sufficient in vivo degradability and excellent anti-adhesion characteristics, and is also superior to conventional ones in terms of handling properties under wet conditions.

The anti-adhesion material 3 according to the third embodiment becomes an anti-adhesion material excellent in antibacterial performance because it contains, in the base layer 12 thereof, an antibacterial agent.

The anti-adhesion material 3 according to the third embodiment has a configuration similar to that of the anti-adhesion material 1 according to the first embodiment except that the base layer contains an antibacterial agent so that it has any relevant advantages among advantages which the anti-adhesion material 1 according to the first embodiment has.

Fourth Embodiment

Figure 4:
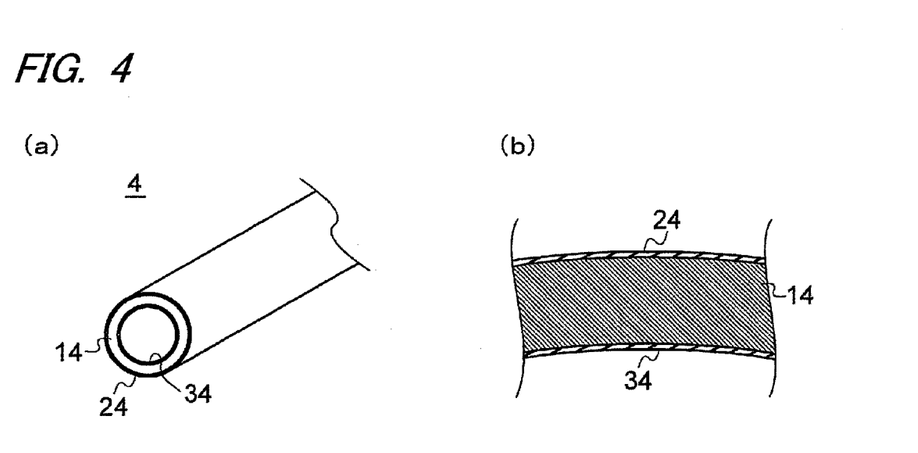

FIG. 4 includes diagrams for describing an anti-adhesion material 4 according to a fourth embodiment, in which FIG. 4(a) is a perspective view of the anti-adhesion material 4 and FIG. 4(b) is a partially enlarged cross-sectional view of the anti-adhesion material 4. In FIGS. 4(a) and 4(b), the layer thickness of a base layer 14 and the layer thicknesses of a first cover layer 24 and a second cover layer 34 relative to the base layer 14 are exaggerated to some extent to facilitate understanding of the present invention.

The anti-adhesion material 4 according to the fourth embodiment has, as shown in FIG. 4, a base layer 14 in cylindrical form, a first cover layer 24 placed on an outer surface of the base layer 14, and a second cover layer 34 placed on an inner surface of the base layer 14.

The base layer 14 is composed of a water soluble polymer. Examples of the water soluble polymer are similar to those of the base layer 10 described in the first embodiment.

The layer thickness of the base layer 14 is set to be, for example, 1 μm to 5000 μm.

The first cover layer 24 and the second cover layer 34 as the cover layer are each composed of an aliphatic ester. Examples of the aliphatic ester are similar to those of the first cover layer 20 and the second cover layer 30 described in the first embodiment.

The optical thickness of each of the first cover layer 24 and the second cover layer 34 as measured using a spectroscopic ellipsometer with a wavelength of 380 nm to 900 nm is set to be 27 nm or greater and smaller than 160 nm (130 nm or greater and smaller than 820 nm in terms of the layer thickness when formed as a layer).

The optical thickness of each of the first cover layer 24 and the second cover layer 34 as measured using a spectroscopic ellipsometer with a wavelength of 380 nm to 900 nm is more preferably 27 nm or greater but not greater than 128 nm (130 nm or greater but not greater than 660 nm in terms of the layer thickness when formed as a layer).

Thus, the anti-adhesion material 4 according to the fourth embodiment having such a configuration has, as in the case of the anti-adhesion material 1 according to the first embodiment, improved handling properties under wet conditions compared with anti-adhesion materials composed only of a base layer containing a water soluble polymer, because the first cover layer 24 and the second cover layer 34 containing an aliphatic ester are placed on the outer surface and the inner surface of the base layer 14 containing a water soluble polymer, respectively. In addition, the optical thickness of the first cover layer 24 and the second cover layer 34 as measured using a spectroscopic ellipsometer with a wavelength of 380 nm to 900 nm is set to be very small, which is 27 nm or greater and smaller than 160 nm (130 nm or greater and smaller than 820 nm in terms of the layer thickness when formed as a layer) so that the anti-adhesion material thus obtained has in vivo degradability sufficiently satisfying the required level and at the same time, has anti-adhesion characteristics comparable to that of anti-adhesion materials composed only of a base layer containing a water soluble polymer.

The anti-adhesion material 4 according to the fourth embodiment therefore has sufficient in vivo degradability and excellent anti-adhesion characteristics, and is also superior to conventional ones in terms of handling properties under wet conditions.

In the anti-adhesion material 4 according to the fourth embodiment, the optical thickness of each of the first cover layer 24 and the second cover layer 34 as measured using a spectroscopic ellipsometer with a wavelength of 380 nm to 900 nm is set to be 27 nm or greater and smaller than 160 nm (130 nm or greater and smaller than 820 nm in terms of the layer thickness when formed as a layer) so that the anti-adhesion material produces the above-described advantage and at the same time, shows significantly improved adhesion between the anti-adhesion material 4 and body tissues when the anti-adhesion material 4 is applied to (placed on) the body tissues.

Furthermore, the anti-adhesion material 4 according to the fourth embodiment is cylindrical so that it is particularly useful as an anti-adhesion material to be used around tubular tissues such as tendons, nerves, and uterine tubes.

The anti-adhesion materials of the present invention have been described based on the above-described embodiments. The present invention is however not limited to or by these embodiments and can be carried out in various modes without departing from the gist of the invention. For example, the following modifications can be made.

(1) The first cover layer and the second cover layer are made of the same aliphatic ester in the first embodiment, the third embodiment, and the fourth embodiment, but the present invention is not limited to it. Alternatively, the first cover layer and the second cover layer may be made of different aliphatic esters, respectively. In this case, it is possible to provide an anti-adhesion material having different functions depending on the surface.

(2) In the anti-adhesion material described in the third embodiment, the base layer contains the antibacterial agent, but the present invention is not limited to it. For example, not the base layer but the cover layer may contain the antibacterial agent or the base layer and the cover layer both contain the antibacterial agent. When the cover layer is made of two layers, that is, a first cover layer and a second cover layer, either one of the first cover layer or the second cover layer may contain the antibacterial agent or both of the first cover layer and the second cover layer may contain the antibacterial agent.

Moreover, the anti-adhesion material described in the third embodiment contains the antibacterial agent as a medical agent, but the present invention is not limited to it. Medical agents other than the antibacterial agent (e.g., antibiotics, anti-inflammatory agents, anti-adhesion agents, anti-cancer agents, disinfectants, and the like) may be used. When at least two of the layers of the anti-adhesion material contain a medical agent, they may contain the same medical agent or contain different medical agents.

(3) The anti-adhesion material described in the fourth embodiment has the first cover layer 24 and the second cover layer 34 on the outer surface and the inner surface of the base layer 14, respectively, but the present invention is not limited to it. As in the second embodiment, the cover layer may be placed only on one of the outer surface and the inner surface of the base layer 14.

In the anti-adhesion material according to the fourth embodiment, none of the base layer 14, the first cover layer 24, and the second cover layer 34 contains a medical agent, but the present invention is not limited to it. As in the third embodiment, the base layer may contain a medical agent or another layer may contain a medical agent.

(4) In the first embodiment, a so-called dipping method is employed in the cover layer forming step, but the present invention is not limited to it. For example, known film formation processes such as spray method may be employed.

EXAMPLES

The present invention will next be described more specifically by means of Example and Comparative Example. The present invention is however not limited to or by them unless it departs from the gist of the invention.

Example

Based on the above-described configuration of the anti-adhesion material 1 according to the first embodiment, a sheet-like base layer having on both surfaces thereof a first cover layer and a second cover layer (hereinafter, may simply be referred to as "cover layers") made of the same material, respectively, was used as an anti-adhesion material of Example.

Described specifically, first, a 100 mm×100 mm×40 μm thick pullulan film was formed as a base layer. A (polylactic acid-polyglycolic acid-poly(ε)caprolactone)/toluene solution (hereinafter, referred to as "coating solution") having a predetermined concentration was prepared. The base layer was dipped in the coating solution to form cover layers on both surfaces of the base layer, respectively. After dipping, the resulting base layer was dried overnight at room temperature and provided as a sample of Example.

Comparative Example

An anti-adhesion material composed only of a base layer containing a water soluble polymer was used as Comparative Example. Described specifically, hyaluronic acid and carboxymethyl cellulose were crosslinked with carbodiimide hydrochloride and the resulting product was formed into a sheet. The resulting sheet was provided as a sample of Comparative Example.

[Calculation Method of Layer Thickness of Cover Layers]

The layer thickness of the cover layers formed on the base layer was calculated in the following procedure.

First, the layer thickness of the single base layer was measured in advance. Then, after forming cover layers on both surfaces of the base layer, respectively, the total thickness of the resulting sample was measured. The layer thickness of the base layer measured in advance was subtracted from the total thickness of the sample to find the total thickness of the cover layers (sum of the layer thicknesses of the first cover layer and the second cover layer). The total thickness of the cover layers was divided by 2 to determine the layer thickness (layer thickness of each of the first cover layer and the second cover layer) of each of the cover layers formed on the base layer.

The layer thickness of the base layer and the total thickness of the sample were measured using Digimatic Indicator ("ID-N112", product of Mitutoyo Corporation).

[Measuring Method of Optical Thickness of Cover Layers]

The optical thickness of the cover layers formed on the base layer was measured by using a spectroscopic ellipsometer ("alpha-SE" (U.S. registered trademark), product of J.A. Woollam Japan Co., Inc.). It was measured with a wavelength of 380 nm to 900 nm.

[Relationship Between Concentration of Coating Solution and Layer Thickness of Cover Layers]

In order to find the relationship between the concentration of a coating solution in which a pullulan film (base layer) is to be dipped and the layer thickness (layer thickness of each of the first cover layer and the second cover layer) of each of the cover layers in the sample after dipping, the present inventors made the following test.

First, a 100 mm×100 mm×40 μm thick pullulan film (base layer) was prepared. The resulting pullulan film was dipped in each of the coating solutions having a concentration gradated between 0.05 w/v % and 5 w/v %. The layer thickness of each of the cover layers (first cover layer and second cover layer) of the sample after dipping was calculated based on the above-described "calculation method of layer thickness of cover layers".

Figure 5:
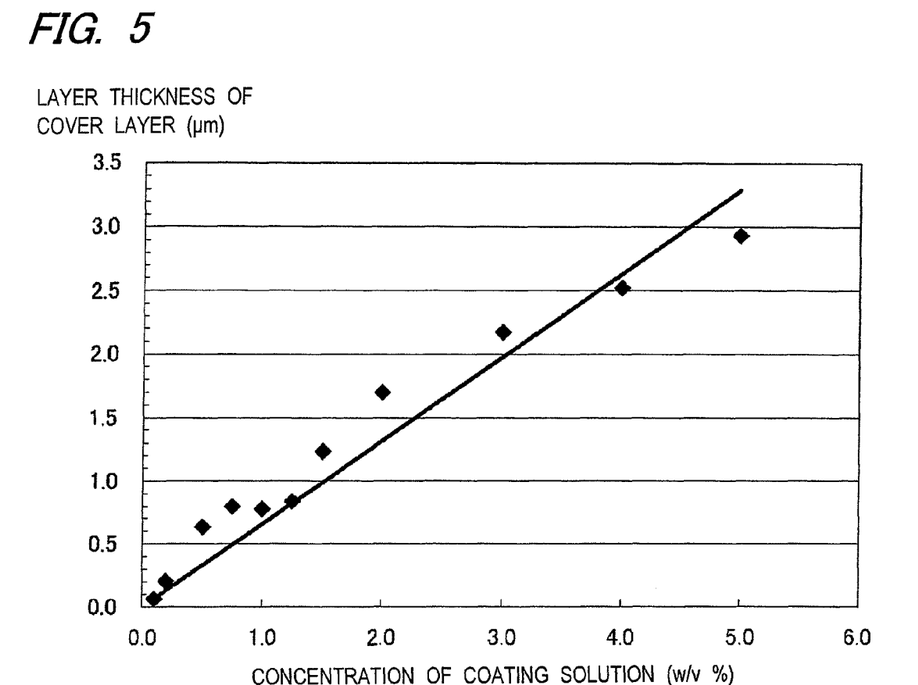
FIG. 5 is a correlation diagram between the concentration of a coating solution and the layer thickness of a cover layer.

FIG. 5 is a correlation diagram between the concentration of a coating solution and the thickness of cover layers.

As is apparent from FIG. 5, it has been found from the results of the above test that there is a strong correlation between the concentration of a coating solution and the layer thickness of cover layers of the sample after dipping. As the layer thickness of cover layers of each sample to be used in Tests 1 to 4, not a value calculated based on "calculation method of layer thickness of cover layers" but a theoretical value determined by obtaining in advance a correlation equation derived from the correlation between the concentration of a coating solution and the layer thickness of cover layers, for example, a linear equation (y=0.66x, x: concentration (w/v %) of a coating solution, y: layer thickness (μm) of cover layers) and substituting, in the equation, the actual concentration of the coating solution when the sample was prepared was used.

[Relationship Between Concentration of Coating Solution and Optical Thickness of Cover Layers]

In order to find the relationship between the concentration of a coating solution in which the pullulan film (base layer) is to be dipped and the optical thickness of each of cover layers (optical thickness of each of the first cover layer and the second cover layer) of the sample after dipping, the present inventors made the following test.

First, seven 100 mm×120 mm×40 μm thick pullulan films (base layers) were prepared. The resulting pullulan films were dipped in each of coating solutions having a concentration gradated between 0.3 w/v % and 0.9 w/v % to prepare samples. The concentration of the coating solution was changed in 7 stages, with an increment of 0.1 w/v %. The optical thickness of the cover layers (the first cover layer and the second cover layer) of the sample after dipping was measured using a spectroscopic ellipsometer.

Figure 6:
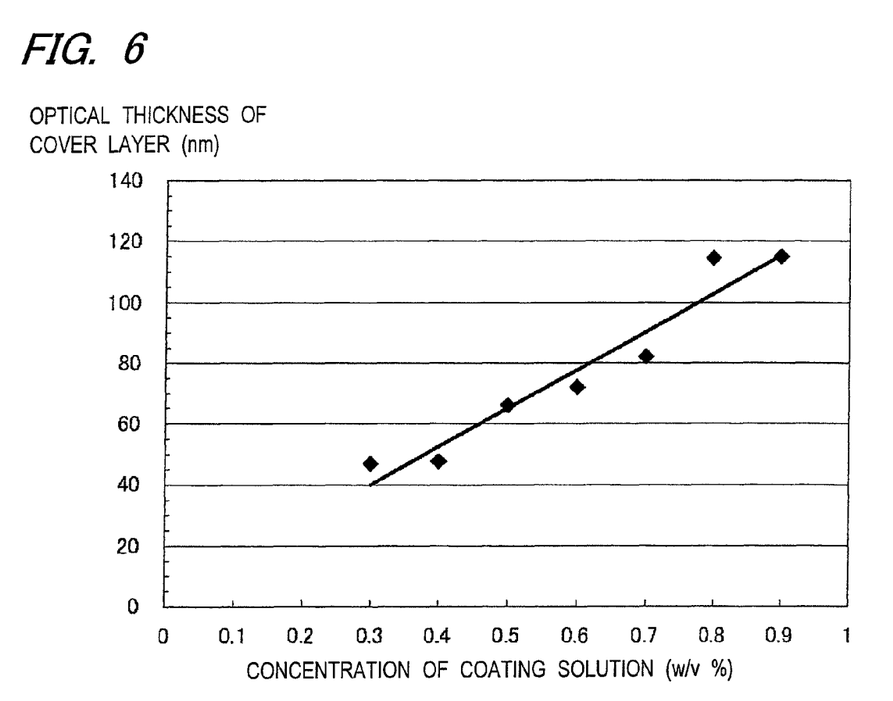
FIG. 6 is a correlation diagram between the concentration of a coating solution and the optical thickness of a cover layer.

FIG. 6 is a correlation diagram between the concentration of a coating solution and an optical thickness of cover layers.

As is apparent from FIG. 6, it has been found from the results of the above test that there is a strong correlation between the concentration of the coating solution and the optical thickness of cover layers at least under the above conditions. As the optical thickness of the cover layers of each sample to be used in Tests 1 to 4, not an actual value measured using the ellipsometer but a theoretical value determined by obtaining in advance a correlation equation derived from the relationship between the concentration of the coating solution and the optical thickness of cover layers, for example, a linear equation (y=126.41x+1.92, x: concentration (w/v %) of a coating solution, y: optical thickness (nm) of cover layers), and substituting, in the equation, the actual concentration of the coating solution when the sample was prepared was used.

[Test 1]

Test 1 is conducted for evaluating degradability of an anti-adhesion material applied to body tissues. The degradability of an anti-adhesion material was evaluated by preparing a test piece from each of the samples obtained in Example and Comparative Example, dipping the test piece in a phosphate buffer, observing the appearance of it, and indicating it by scores.

(1) Preparation of Test Piece

Each of the samples obtained in Example and Comparative Example was cut into 50 mm×50 mm square test pieces. As the sample obtained in Example, samples (Samples A-1 to A-8) were prepared, respectively, while setting the concentration of a coating solution at eight stages, that is, 0.05 w/v %, 0.10 w/v %, 0.20 w/v %, 0.50 w/v %, 0.75 w/v %, 1.00 w/v %, 1.25 w/v %, and 1.50 w/v %. From each of these samples, five test pieces were prepared. Also from the sample (Sample A-0) obtained in Comparative Example, five test pieces were prepared.

(2) Testing Method

First, a test piece was sandwiched, at both sides thereof, with a mesh having a pore size of 40 μm. The test piece sandwiched with the mesh was dipped in a phosphate buffer (37° C., adjusted to pH 7.4) contained in a beaker and gently shaken continuously (at 50 rpm). Fourteen days after dipping was started, the appearance of the test piece was observed and the degree of degradation (degradation state) of the test piece was indicated by scores. With regard to the score (hereinafter, degradability score), a test piece which maintained its shape was indicated by "Score 2", a test piece which did not maintain its shape but had remnants was indicated by "Score 1", and a test piece which did not maintain its shape and had no remnant was indicated by "Score 0". Based on the degradability scores of five test pieces, an average degradability score was calculated.

Figure 7:
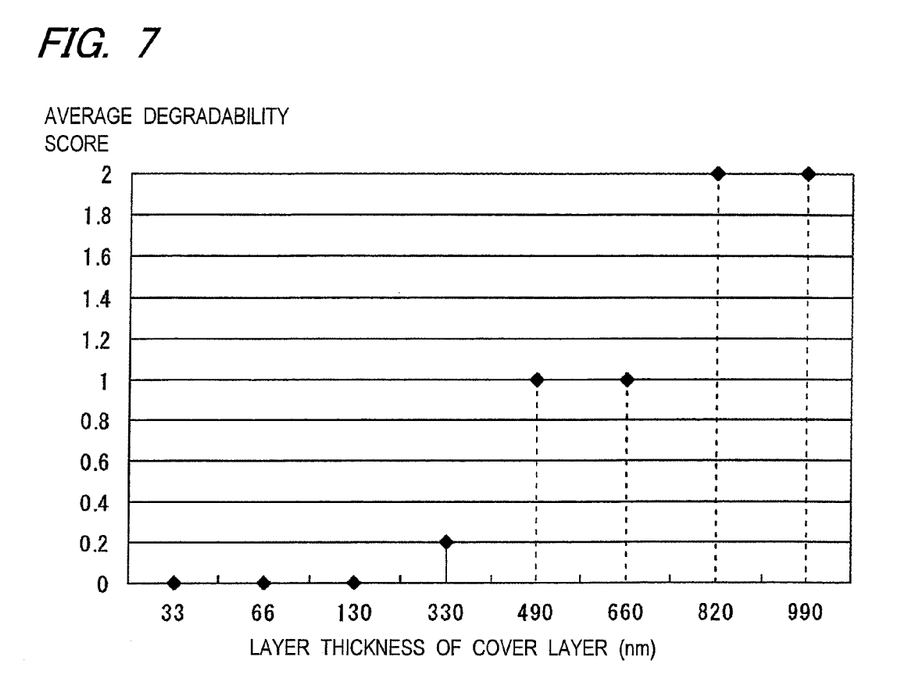
FIG. 7 is a diagram showing the relationship between the layer thickness of a cover layer and an average degradability score.

The thicknesses (theoretical value of layer thickness and theoretical value of optical thickness) of the cover layers and average degradability score of each sample are shown in Table 1. In addition, the relationship between the layer thickness (theoretical value) of cover layers and the average degradability score is shown in FIG. 7.

to have certain degradability. In particular, Samples A-1 to A-4 were found to have degradability comparable to that of Sample A-0 (Comparative Example). As a result, it has been confirmed that sufficient in vivo degradability can be achieved by forming cover layers such that the layer thickness thereof is set to be less than 820 nm (i.e., the optical thickness being less than 160 nm); higher degradability can be achieved by forming cover layers such that the layer thickness thereof is set to be 660 nm or less (i.e., the optical thickness being 128 nm or less); and degradability comparable to that of conventional anti-adhesion materials can be achieved by forming cover layers such that the layer thickness thereof is set to be less than 490 nm (i.e., the optical thickness being less than 97 nm).

As is apparent from Table 1, the optical thickness of each cover layer as measured using a spectroscopic ellipsometer is smaller than the layer thickness of the cover layer, which is presumed to occur because the cover layers formed on the base layer penetrate through the surface of the base layer and each cover layer is integrated with the boundary with the base layer.

[Test 2]

Test 2 is conducted for evaluating the anti-adhesion characteristics of an anti-adhesion material. The anti-adhesion characteristics was evaluated by preparing test pieces from the samples obtained in Example and Comparative Example, applying each of the test pieces to the abdominal cavity of a rat, observing the degree of adhesion, and indicating the degree by scores.

(1) Preparation of Test Piece

Each of the samples obtained in Example and Comparative Example was cut into 30 mm×30 mm square test pieces. As the sample relating to Example, a sample (Sample B-1) prepared by setting the concentration of a coating solution at 0.5 w/v % was used and ten test pieces were prepared from it. Also from the sample (Sample B-0) relating to Comparative Example, ten test pieces were prepared.

(2-1) Testing Method (Preparation of Adhesion Model)

First, a rat underwent laparotomy by abdominal median incision under general anesthesia for external exposure of the appendix. Then, a predetermined area (1 to 2 cm²) of the exposed appendix on the side of the small intestine was abraded with sterile gauze until petechiae occurred. After petechiae occurred, the appendix was exposed to the air for exactly 10 minutes. The test piece was applied to the abraded site and the appendix was then returned in the abdominal cavity. The abdominal wall incision was closed in two layers by continuously suturing with an absorbable suture (3-0).

TABLE 1

| Sample No. | Concentration (w/v %) of coating solution | Layer thickness (nm) of first and second cover layers | Optical thickness (nm) of first and second cover layers | Average degradability score |
|---|---|---|---|---|
| A-1 | 0.05 | 33 | 8 | 0 |
| A-2 | 0.10 | 66 | 15 | 0 |
| A-3 | 0.20 | 130 | 27 | 0 |
| A-4 | 0.50 | 330 | 65 | 0.2 |
| A-5 | 0.75 | 490 | 97 | 1 |
| A-6 | 1.00 | 660 | 128 | 1 |
| A-7 | 1.25 | 820 | 160 | 2 |
| A-8 | 1.50 | 990 | 192 | 2 |
| A-0 | — | — | — | 0 |

As shown in Table 1 and FIG. 7, Samples A-7 and A-8 were inferior in degradability, but Samples A-1 to A-6 were found For each of the sample (Sample B-1) relating to Example and the sample (Sample B-0) relating to Comparative Example, ten adhesion models were prepared per group, while ten models in total were prepared for control group (the appendix not applied with the test piece but only abraded).

(2-2) Testing Method (Observation of Adhesion Degree, Calculation of Adhesion Score)

Fourteen days after preparation of the model, a rat underwent laparotomy under general anesthesia and the degree of adhesion at an adhesion induced site (the site to which a test piece was applied and therearound) was observed with the naked eye and was indicated by scores. With regard to the score (hereinafter, adhesion score), a model from which no adhesion was observed was indicated by "Score 0"; a model from which thin and easily separable adhesion was observed was indicated by "Score 1"; a model from which adhesion weak but strong enough for light traction was observed though in a narrow range was indicated by "Score 2"; a model from which considerably firm adhesion was observed or adhesion was observed at at least two sites was indicated by "Score 3"; and a model from which adhesion was observed at three or more sites was indicated by "Score 4".

(3) Judgment of Significant Difference

Average adhesion score of each of samples relating to Control group, Example, and Comparative Example was calculated and a significant test was conducted between control group and Example and between Example and Comparative Example. The Wilcoxon rank sum test was employed as the test and a significant difference was judged with a risk rate of 5% or less as a level of significance (p-value≤0.05).

Figure 8:
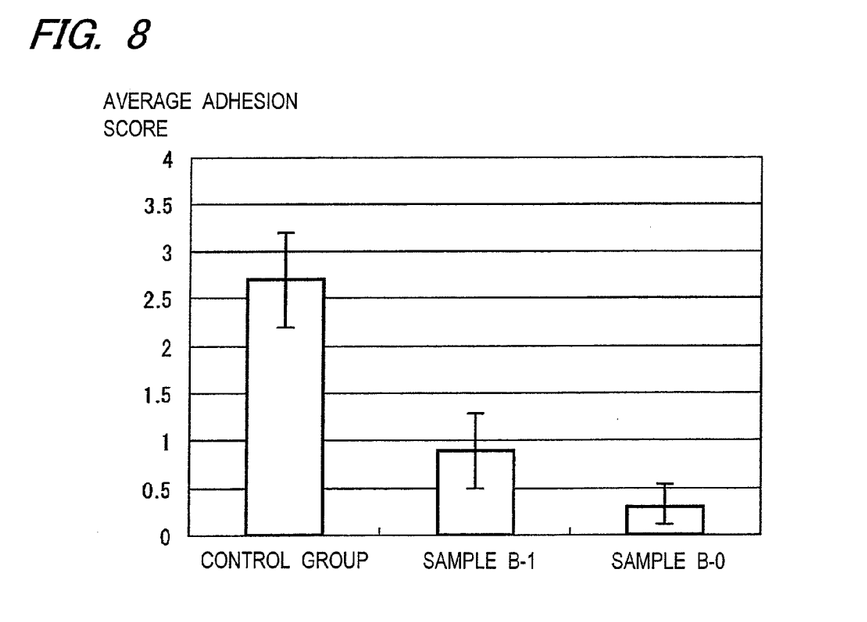
FIG. 8 shows an average adhesion score of each of Control group, Sample B-1, and Sample B-0.

The adhesion score and average adhesion score of each of the adhesion models are shown in Table 2. In addition, the average adhesion score of Control group and Samples B-1 and B-0 are shown in FIG. 8.

TABLE 2

| | Animal No. | Adhesion score | Average adhesion score |
|---|---|---|---|
| Control group | 101 | 4 | 2.7 |
| | 102 | 3 | (±S.E. 0.5) |
| | 103 | 4 | |
| | 104 | 3 | |
| | 105 | 2 | |
| | 106 | 3 | |
| | 107 | 0 | |
| | 108 | 4 | |
| | 109 | 0 | |
| | 110 | 4 | |
| Sample B-1 | 201 | 0 | 0.9 |
| | 202 | 0 | (±S.E. 0.4) |
| | 203 | 0 | |
| | 204 | 0 | |
| | 205 | 2 | |
| | 206 | 2 | |
| | 207 | 2 | |
| | 208 | 0 | |
| | 209 | 3 | |
| | 210 | 0 | |
| Sample B-0 | 301 | 0 | 0.3 |
| | 302 | 0 | (±S.E. 0.2) |
| | 303 | 2 | |
| | 304 | 0 | |
| | 305 | 1 | |
| | 306 | 0 | |
| | 307 | 0 | |
| | 308 | 0 | |
| | 309 | 0 | |
| | 310 | — (*) | |

(*) died on the next day after preparation of the model

As shown in Table 2 and FIG. 8, the average adhesion score of Sample B-1 was smaller than that of Control group. Statically, a risk rate was 5% (p-value=0.05) and a significant difference was recognized between them. No statically significant difference was recognized between the average adhesion score of Sample B-1 (Example) and the average adhesion score of Sample B-0 (Comparative Example). This suggests that the anti-adhesion material of the present invention has excellent anti-adhesion characteristics when used for 14 days and the anti-adhesion characteristics is comparable to that of a conventional anti-adhesion material.

[Test 3]

Test 3 is conducted for evaluating handling properties of an anti-adhesion material when it is wet. In evaluating the handling properties of an anti-adhesion material when it is wet, a test piece was prepared from the samples relating to Example and Comparative Example; breaking strength of the resulting test piece when it was partially wetted was measured; and the handling properties of the test piece when it is wet were valuated based on the measurement results.

(1) Preparation of Test Piece

Samples relating to Example and Comparative Example were each cut into strip-shaped test pieces 10 mm wide and about 100 mm long. As the sample relating to Example, samples (Samples C-1 to C-4) prepared, respectively, by setting the concentration of a coating solution at four stages, that is, 0.10 w/v %, 0.20 w/v %, 0.50 w/v %, and 0.75 w/v % were used and from each of the samples, five test pieces were prepared. Also from the sample (Sample C-0) relating to Comparative Example, five test pieces were prepared.

(2) Testing Method

Each of the test pieces was held at both end portions thereof (both end portions in the longer direction) and looped. The looped portion (intermediate portion of the test piece) was pressed against a pseudo wet tissue for 30 seconds. At this time, the length of the looped portion to be pressed against the pseudo wet tissue was set at about 10 mm. As the pseudo wet tissue, 100 mm×140 mm "BELL CLEAN" (trade mark of Aion Co., Ltd.) which had been caused to absorb about 30 mL of ultrapure water was used.

Next, the test piece was removed from the pseudo wet tissue and set in a tensile tester ("Autograph AGS-J", product of Shimadzu Corporation) to measure the breaking strength of the test piece. Time required from the removal of the test piece from the pseudo wet tissue to the measurement of the breaking strength was set within 10 seconds.

Figure 9:
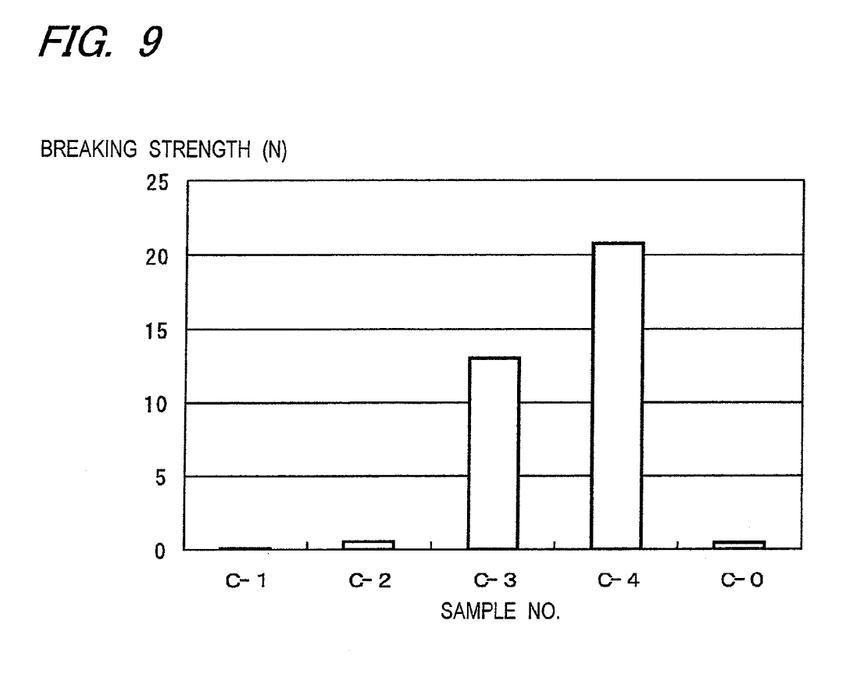
FIG. 9 shows measurement results of breaking strength of each sample.

Measurement results of the breaking strength of each sample are shown in Table 3 and FIG. 9.

TABLE 3

| Sample No. | Concentration (w/v %) of coating solution | Layer thickness (nm) of first and second cover layers | Optical thickness (nm) of first and second layers | Breaking strength, Average (N) |
|---|---|---|---|---|
| C-1 | 0.10 | 66 | 15 | 0.064 |
| C-2 | 0.20 | 130 | 27 | 0.561 |
| C-3 | 0.50 | 330 | 65 | 13.011 |
| C-4 | 0.75 | 490 | 97 | 20.721 |
| C-0 | — | — | — | 0.441 |

As shown in Table 3 and FIG. 9, the breaking strength of the samples C-2, C-3, and C-4 having cover layers with a layer thickness of 130 nm or greater (i.e., 27 nm or greater in terms of optical thickness) was higher than the breaking strength of the sample C-0 (Comparative Example). It has therefore been confirmed that by setting the layer thickness of cover layers to be applied at 130 nm or greater (i.e., 27 nm or greater in terms of optical thickness of the cover layers), the resulting anti-adhesion material has a greater breaking strength under wet conditions, i.e., is superior in terms of handling properties under set conditions, as compared with the conventional anti-adhesion materials.

[Conclusion of Tests 1 to 3]

It can be confirmed from Test 1 that by setting the layer thickness of the cover layers at less than 820 nm (less than 160 nm in terms of optical thickness of the cover layers), the resulting anti-adhesion material has sufficient in vivo degradability. In addition, it can be confirmed from Test 2 that the anti-adhesion material according to Example shows excellent anti-adhesion characteristics when used for 14 days and its anti-adhesion characteristics is comparable to that of the conventional anti-adhesion material. Furthermore, it can be confirmed from Test 3 that by setting the layer thickness of the cover layers obtained by application at 130 nm or greater (i.e., 27 nm or greater in terms of the optical thickness of the cover layers), the resulting anti-adhesion material is superior to the conventional anti-adhesion materials in terms of handling properties under wet conditions.

It can therefore be confirmed that an anti-adhesion material which has a base layer containing a water soluble polymer and on at least one of both surfaces thereof, a cover layer containing an aliphatic ester and in which the cover layer to be formed has a layer thickness of 130 nm or greater and smaller than 820 nm (i.e., 27 nm or greater and smaller than 160 nm in terms of the optical thickness of the cover layer) has sufficient in vivo degradability and excellent anti-adhesion characteristics, and is also superior to the conventional ones in terms of handling properties.

[Test 4]

In addition to the above Tests 1 to 3, the present inventors also made a test for evaluating adhesion of an anti-adhesion material applied to body tissue. In evaluating the adhesion of an anti-adhesion material, a test piece was prepared from the respective samples relating to Example and Comparative Example and frictional resistance (adhesive strength) when the test piece in contact with a pseudo wet tissue was stretched was measured. Based on the measurement results, the adhesion of the anti-adhesion material was evaluated.

(1) Preparation of Test Piece

Each of the samples relating to Example and Comparative Example was cut into strip-shaped test pieces 10 mm wide and about 100 mm long. As the sample relating to Example, samples (Samples D-1 to D-11) were prepared, respectively, by setting the concentration of a coating solution at 11 stages, that is, 0.10 w/v %, 0.20 w/v %, 0.50 w/v %, 0.75 w/v %, 1.00 w/v %, 1.25 w/v %, 1.50 w/v %, 2.00 w/v %, 3.00 w/v %, 4.00 w/v %, and 5.00 w/v % were used and from each of the samples, five test pieces were prepared. Also from the sample (Sample D-0) relating to Comparative Example, five test pieces were prepared.

(2) Testing Method

One end portion, in a longer direction, of the test piece was inserted in a fixing jig equipped with a push pull gauge and a 40-mm portion of the test piece from the end of the other end portion was pressed against a pseudo wet tissue for 10 seconds. As the pseudo wet tissue, 100 mm×140 mm "BELL CLEAN" (trade mark of Aion Co., Ltd.) which had been caused to absorb about 30 mL of ultrapure water was used.

Next, the test piece together with the fixing jig was stretched (1 mm/1 sec) along the longer direction while bringing the test piece into contact with the pseudo wet tissue to measure the frictional resistance of the test piece.

Figure 10:
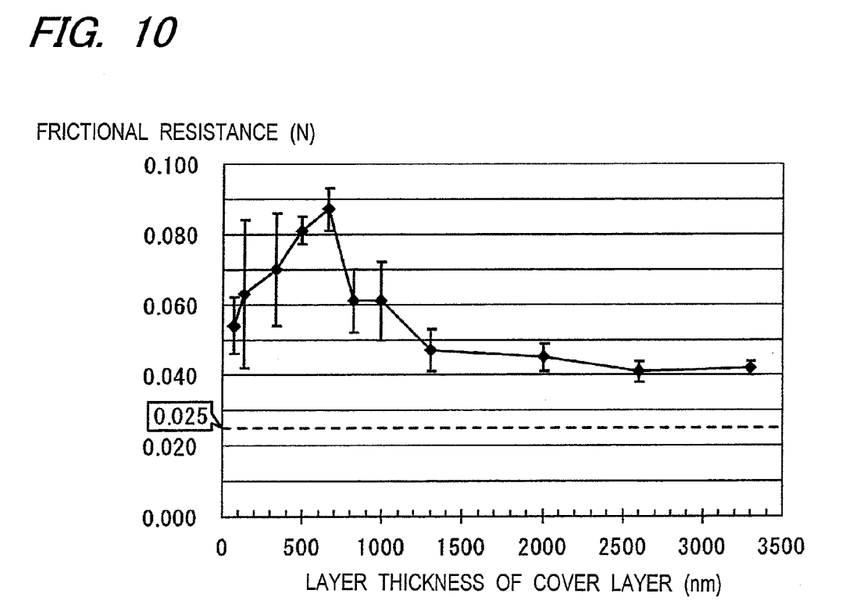
FIG. 10 shows measurement results of frictional resistance of each sample.

Measurement results of the frictional resistance of each sample are shown in Table 4 and FIG. 10.

TABLE 4

| Sample No. | Concentration (w/v %) of coating solution | Layer thickness (nm) of first and second cover layers | Optical thickness (nm) of first and second cover layers | Frictional resistance, Average (N) | Standard deviation |
|---|---|---|---|---|---|
| D-1 | 0.10 | 66 | 15 | 0.054 | 0.008 |
| D-2 | 0.20 | 130 | 27 | 0.063 | 0.021 |
| D-3 | 0.50 | 330 | 65 | 0.07 | 0.016 |
| D-4 | 0.75 | 490 | 97 | 0.081 | 0.004 |
| D-5 | 1.00 | 660 | 128 | 0.087 | 0.006 |
| D-6 | 1.25 | 820 | 160 | 0.061 | 0.009 |
| D-7 | 1.50 | 990 | 192 | 0.061 | 0.011 |
| D-8 | 2.00 | 1300 | 255 | 0.047 | 0.006 |
| D-9 | 3.00 | 2000 | 381 | 0.045 | 0.004 |
| D-10 | 4.00 | 2600 | 508 | 0.041 | 0.003 |
| D-11 | 5.00 | 3300 | 634 | 0.042 | 0.002 |
| D-0 | — | — | — | 0.025 | 0.004 |

As shown in FIG. 4 and FIG. 10, any of the samples D-1 to D-11 relating to Example had frictional resistance greater than that of the sample D-0 relating to Comparative Example. In particular, the samples D-2 to D-7 showed more than twice the frictional resistance of the sample D-0 relating to Comparative Example. It can be confirmed from the results that by setting the layer thickness of the cover layers at 130 nm or greater and smaller than 820 nm (i.e., 27 nm or greater and smaller than 160 nm in terms of the optical thickness of the cover layers), the resulting anti-adhesion material has far greater adhesive strength than that of the conventional anti-adhesion material, making it possible to significantly improve the adhesion between the anti-adhesion material and body tissue when the anti-adhesion material is applied to the body tissue compared with the conventional anti-adhesion material.

While the present invention has been described in detail with reference to certain embodiments, it is apparent for those skilled in the art that various changes or modifications can be made therein without departing from the spirit and scope of the present invention. The present application is based on Japanese Patent Application filed on Dec. 28, 2009 (Japanese Patent Application No. 2009-296876), the content of which is incorporated herein by reference.

INDUSTRIAL APPLICABILITY

The anti-adhesion material of the present invention is suited for use as a functional medical material to be used during operation or treatment of injury because it has sufficient in vivo degradability and excellent anti-adhesion characteristics and is excellent in terms of handling properties when it is wet.

EXPLANATION OF REFERENCE NUMERALS 1 to 4 Anti-adhesion material
10, 12, 14 Base layer
22 Cover layer
20, 24 First cover layer
30, 34 Second cover layer

The invention claimed is:

1. An anti-adhesion material comprising:
a base layer containing a water soluble polymer; and
a cover layer containing an aliphatic ester and placed on at least one of both surfaces of the base layer,
wherein an optical thickness of the cover layer, as measured using a spectroscopic ellipsometer with a wavelength of 380 nm to 900 nm, is 27 nm or greater but not greater than 128 nm.

2. An anti-adhesion material comprising a base layer containing a water-soluble polymer wherein, on at least one of both surfaces of said base layer, a cover layer containing an aliphatic ester has been placed, and a layer thickness of the cover layer is 130 nm or greater but not greater than 660 nm.

3. The anti-adhesion material according to claim 1, wherein the cover layer comprises a first cover layer placed on one of the surfaces of the base layer and a second cover layer placed on the other of the surfaces of the base layer, and
wherein the first cover layer and the second cover layer are made of a same material.

4. The anti-adhesion material according to claim 1, wherein the cover layer comprises a first cover layer placed on one of the surfaces of the base layer and a second cover layer placed on the other of the surfaces of the base layer, and
wherein the first cover layer and the second cover layer are made of different materials.

5. The anti-adhesion material according to claim 1, wherein at least one of the base layer and the cover layer contains a medical agent.

6. The anti-adhesion material according to claim 1, wherein the water soluble polymer is a polysaccharide, protein or synthetic polymer.

7. The anti-adhesion material according to claim 2, wherein the cover layer comprises a first cover layer placed on one of the surfaces of the base layer and a second cover layer placed on the other of the surfaces of the base layer, and
wherein the first cover layer and the second cover layer are made of a same material.

8. The anti-adhesion material according to claim 2, wherein the cover layer comprises a first cover layer placed on one of the surfaces of the base layer and a second cover layer placed on the other of the surfaces of the base layer, and
wherein the first cover layer and the second cover layer are made of different materials.

9. The anti-adhesion material according to claim 2, wherein at least one of the base layer and the cover layer contains a medical agent.

10. The anti-adhesion material according to claim 2, wherein the water soluble polymer is a polysaccharide, protein or synthetic polymer.

11. The anti-adhesion material according to claim 1, wherein a layer thickness of the base layer is 1 μm to 5000 μm.

12. The anti-adhesion material according to claim 2, wherein a layer thickness of the base layer is 1 μm to 5000 μm.

* * * * *